(12) United States Patent
Dinarello et al.

(10) Patent No.: US 8,637,702 B2
(45) Date of Patent: Jan. 28, 2014

(54) DERIVATIVES OF N-HYDROXYBENZAMIDE FOR TREATING HIV INFECTIONS

(75) Inventors: Charles Dinarello, Boulder, CO (US); Gianluca Fossati, Milan (IT); Paolo Mascagni, Villasanta (IT)

(73) Assignee: Italfarmaco S.p.A., Milan (IT)

(*) Notice: Subject to any disclaimer, the term of this patent is extended or adjusted under 35 U.S.C. 154(b) by 0 days.

(21) Appl. No.: 13/393,863

(22) PCT Filed: Sep. 14, 2010
(Under 37 CFR 1.47)

(86) PCT No.: PCT/IB2010/054139
§ 371 (c)(1),
(2), (4) Date: Apr. 11, 2012

(87) PCT Pub. No.: WO2011/048514
PCT Pub. Date: Apr. 28, 2011

(65) Prior Publication Data
US 2012/0203014 A1    Aug. 9, 2012

(30) Foreign Application Priority Data
Oct. 23, 2009  (IT) .............................. MI2009A1837

(51) Int. Cl.
*C07C 259/04*  (2006.01)
*C07D 317/04*  (2006.01)

(52) U.S. Cl.
USPC .......................................... 562/622; 549/436

(58) Field of Classification Search
USPC .......................................... 549/436; 562/622
See application file for complete search history.

(56) References Cited

U.S. PATENT DOCUMENTS 7,635,788 B2 * 12/2009 Pinori et al. ................... 562/622

FOREIGN PATENT DOCUMENTS

| WO | WO 97/43251 A1 | 11/1997 |
| WO | WO 2004/063146 A1 | 7/2004 |
| WO | WO 2004/065355 A1 | 8/2004 |
| WO | WO 2006/003068 A2 | 1/2006 |
| WO | WO 2008/097654 A1 | 8/2008 |

OTHER PUBLICATIONS

Wanchu et al. Immunology Letters 74 (2000) 121-12.*
Smith, AIDS treatment news (1996), (No. 242), 3-4.*
Paris, M., et al; "Additions and Corrections"; *J. Med. Chem.*, vol. 51, p. 3330 (2008).
Imamichi, H., et al; "Human Immunodeficiency Virus Type 1 Quasi Species That Rebound after Discontinuation of Highly Active Antiretroviral Therapy Are Similar to the Viral Quasi Species Present before Initiation of Therapy"; *The Journal of Infectious Diseases*, vol. 183, pp. 36-50 (2001).
Quivy, V., et al.; Chapter 17, "Chromatin-Associated Regulation of HIV-1 Transcription, Implications for the development of therapeutic strategies"; T.K. Kundu and D. Dasgupta (eds.), *Chromatin and Disease*, pp. 371-396 (2007).
Bi, G., et al; "The Molecular Mechanism of HDAC Inhibitors in Anticancer Effects"; *Cellular & Molecular Immunology*, vol. 3, No. 4, pp. 285-290 (2006).
Blanchard, F., et al; "Histone deacetylase inhibitors: new drugs for the treatment of inflammatory diseases?", *Reviews Drug Discovery Today*, vol. 10, No. 3, pp. 197-204 (2005).
Adcock, I., Commentary "HDAC inhibitors as anti-inflammatory agents", *British Journal of Pharmacology*, vol. 150, pp. 829-831 (2007).
Paris, M., et al; "Histone Deacetylase Inhibitors: From Bench to Clinic"; *Journal of Medicinal Chemistry*, vol. 51, No. 6, pp. 1505-1529 (2008).
Jones, P., et al; "2-Trifluoroacetylthiophenes, a novel series of potent and selective class II histone deacetylase inhibitors"; *Bioorganic & Medicinal Chemistry Letters*, vol. 18, pp. 3456-3461 (2008).
Archin, N.M., et al; "Expression of latent human immunodeficiency type 1 is induced by novel and selective histone deacetylase inhibitors"; *AIDS*, vol. 23, pp. 1799-1806 (2009).
Lehrman, G., et al; "Depletion of latent HIV-1 infection in vivo: a proof-of-concept study"; *The Lancet*, vol. 366, pp. 549-555 (2005).
"2110 Safety and Efficacy of Oral ITF 2357 in Patients with Active Systemic Onset Juvenile Idiopathic Arthritis (SOJIA)—Results of a Phase II, Open label, International, Multicentre Clinical Trial"; *72nd Annual Meeting of the American College of Rheumatology* San Francisco, CA, Oct. 29, 2008, 1 pg.
Nold, M.F., et al; "Endogenous IL-32 Controls Cytokine and HIV-1 Production"; *J. Immunol.* vol. 181, pp. 557-565 (2008).
Monzani, M.V., et al; ITALFARMACO, "Genotoxic Potential of ITF2357, A Novel HDAC Inhibitor", *11 Eurotox 2007 44th Congress of Toxicology poster, Italfarmaco Research Centre*, Via Dei Lavoratori 54, I-20092 Cinisello Balsamo (MI), Italy, 1 pg.
Shehu-Xhilaga, M., et al; "The novel histone deacetylase inhibitors metacept-1 and metacept-3 potently increase HIV-1 transcription in latently infected cells"; *AIDS*, vol. 23, pp. 2047-2059 (2009).
Lehrman, G., et al; "Depletion of latent HIV-1 infection in vivo: a proof-of-concept study"; *Lancet*, vol. 366, pp. 549-555, Aug. 13, 2005 (XP025277982).
Savarino, A., et al; ""Shock and kill" effects of class I-selective histone deacetylase inhibitors in combination with the glutathione synthesis inhibitor buthionine sulfoximine in cell line models for HIV-1 quiescence"; *Retrovirology*, vol. 6, p. 52, Jun. 2, 2009 (XP002584354).
Edelstein, L.C., et al; "Short Communication: Activation of Latent HIV Type 1 Gene Expression by Suberoylanilide Hydroxamic Acid (SAHA), an HDAC Inhibitor Approved for Use to Treat Cutaneous T Cell Lymphoma"; *AIDS Research and Human Retroviruses*, vol. 25, No. 9, pp. 883-887, Sep. 1, 2009 (XP002584355).
Riester, D., et al; "Histone deacetylase inhibitors-turning epigenic mechanisms of gene regulation into tools of therapeutic intervention in malignant and other diseases"; *Applied Microbiology and Biotechnology*, vol. 75, No. 3, pp. 499-514, Mar. 22, 2007 (XP019513732).
Matalon, S., et al; "The Histone Deacetylase Inhibitor ITF2357 Decreases Surface CXCR4 and CCR5 Expression on CD4(+) T-Cells and Monocytes and is Superior to Valproic Acid for Latent HIV-1 Expression in Vitro"; *Journal of Acquired Immune Deficiency Syndromes*, vol. 54, No. 1, May 1, 2010 (XP008122505).

* cited by examiner

*Primary Examiner* — Nizal Chandrakumar
(74) *Attorney, Agent, or Firm* — Nixon & Vanderhye

(57) ABSTRACT

Compound selected from 4-(2(S)-benzoylamino-3-naphthalen-2-yl-propionylamino)-N-hydroxy-benzamide and benzo[1,3]dioxole-5-carboxylic acid [1(S)-(4-hydroxycarbamoylphenylcarbamoyl)-2-naphthalen-2-yl-ethyl]-amide, for use in the treatment of a HIV infection. The compound is administered in combination and/or in temporal proximity with at least one anti-retroviral agent.

10 Claims, No Drawings

DERIVATIVES OF N-HYDROXYBENZAMIDE FOR TREATING HIV INFECTIONS

This application is the U.S. national phase of International Application No. PCT/IB2010/054139 filed 14 Sep. 2010 which designated the U.S. and claims priority to Italian Application No. MI2009A001837 filed 23 Oct. 2009, the entire contents of each of which are hereby incorporated by reference.

The present invention relates to the use of N-hydroxybenzamide-based histone deacetylase inhibitors for treating humans infected by human immunodeficiency virus (HIV). In particular for the treatment of patients with infection of T $CD4^+$ cells due to persistent, latent HIV, in combination with a highly active antiretroviral therapy (HAART), with the aim of eliminating the HIV infection.

PRIOR ART

Since the introduction of the highly active antiretroviral therapy (HAART) more than a decade ago, the HIV-1 infection may be efficiently controlled, maintaining the HIV-1 viremia below the detectable values. However, the elimination of HIV-1 infection through extended HAART therapy is not yet possible. Upon interruption of the HAART, there occurs the viremia rebound, typically after two weeks [Imamichi H. et al. *J. Infect. Dis.* 183, 36 (2001)].

The source of viral rebound is a long-term cell pool, most probably the memory T-cells reservoir which are infected more slowly, which hosts the HIV-1 integrated proviral DNA. Consolidated techniques for quantifying the latent cell pool are available and it is calculated that one memory cell out of a million of an HIV-1 positive patient carries a replication-competent integrated provirus.

The mechanisms that maintain the proviral DNA transcriptionally inactive in quiescent cells are known. However, it has been long believed that the mechanism includes a chromatin-associated regulation [Quivy V. et al. *Subcell Biochem.* 41, 371 (2007)]. In the latent cell, the integrated proviral DNA is densely organised in nucleosomes. The long terminal repeat (LTR) 5' of HIV-1, containing the promoter and enhancer elements, is the target of the binding of numerous transcription factors and it is organized into two nucleosomes (nuc-0 and nuc-1). The NFκB p50 homodimer, as well as AP-4, YY1 and LSF1, recruits the histone deacetylase/s (HDAC) to LTR, which in turn results in the deacetylation of local histones, in the compaction of chromatin, and in the prevention of the binding of RNA-polymerase II.

The HDAC inhibitors (HDACi), a new class of synthetic compounds, may invalidate the enzymatic activity of HDACs and the relative repression of the HIV-1 gene expression. Furthermore, contrary to the NFκB cell activators, like IL-2, OKT3 or TNFα, HDACi may facilitate gene expression without the general activation of the T-cells.

Histone deacetylases (HDACs) are enzymes capable of removing the acetyl group bound to the lysine residues in the N-terminal portion of the histones or in other proteins.

HDACs may be divided into four classes, according to structural homologies. Class I HDACs (HDAC 1, 2, 3 and 8) are similar to the RPD3 yeast protein and they are found in the cell nucleus. Class II HDACs (HDAC 4, 5, 6, 7, 9 and 10) are similar to the HDA1 yeast protein and they are found both in the nucleus and in the cytoplasm. Class III HDACs are a structurally distinct form of NAD-dependent enzymes correlated to the SIR2 yeast protein. Class IV (HDAC 11) currently consists of a single enzyme having particular structural characteristics. Classes I, II and IV HDACs are enzymes containing zinc and they may be inhibited by various molecular classes: hydroxamic acid derivatives, cyclic tetrapeptides, short chain fatty acids, aminobenzamides, electrophilic ketone derivatives, and the like. Class III HDACs are not inhibited by hydroxamic acids, and the inhibitors thereof have structural characteristics different from those of the other classes.

For the purposes of the present invention, the expression "histone deacetylase inhibitor" it is meant to indicate any molecule of natural origin, recombinant or synthetic, capable of inhibiting the activity of at least one of the enzymes classified as class I, II or IV histone deacetylase.

Histone deacetylase inhibitors are a class of molecules having an anti-neoplastic and anti-inflammatory activity.

In tumour cells, the histone deacetylase inhibitors inhibit the cellular proliferation and induce cellular death and differentiation [Gaofeng Bi and Guosheng Jiang in *Cellular & Molecular Immunology* 3, 285-290 (2006)].

Histone deacetylase inhibitors are also capable of modulating the production of cytokines and other pro-inflammatory factors by the immunocompetent cells and they have proven, in vivo, anti-inflammatory properties [Frederic Blanchard and Céline Chipoy in *Drug Discovery Today* 10, 197-204 (2005); I M Adcock in *British Journal of Pharmacology* 150, 829-831 (2007)].

Numerous clinical studies that use various inhibitors, both for tumour diseases and for inflammatory diseases, are currently in progress, and they are at different stages of progress [Marielle Paris et al. in *Journal of Medicinal Chemistry* 51, 1505-1529 (2008)].

Diethyl-[6-(4-hydroxycarbamoyl-phenylcarbamoyloxymethyl)-naphtalen-2-yl-methyl]ammonium chloride, which is described in WO 97/43251 (anhydrous form) and in WO 2004/065355 (monohydrate crystal form), both incorporated herein by reference, is a HDACs inhibitor with good anti-inflammatory activity; the monohydrate crystal form of such an active ingredient is also known as ITF2357 and/or Givinostat.

Other 4-Amino-N-hydroxy-hydroxybenzamide derivatives, capable of inhibiting HDAC enzymes, are disclosed in WO 2004/063146 and WO 2006/003068, both incorporated herein by reference.

Various HDAC inhibitors were proven capable of inducing the HIV-1 gene expression from a latently infected cell line; however, concerns about possible toxic effect of the inhibitors, at the concentration required for performing the induction, have been raised [Shehu-Xhilaga, M. et al. *AIDS* 23, 2047 (2009)]; regarding this, is it has been recently proposed [Archin, N M et al. *AIDS* 23, 1799 (2009)] that selective Class I HDAC inhibitors could be potent inducers of HIV with lower cytotoxicity.

Valproic acid (VPA), a carboxylic acid HDACi, prescribed for convulsive and mental disorders, was combined with HAART in some clinical studies but without leading to any considerable diminution of the latent reservoir [Lehrman G et al. *Lancet* 366 (9485), 549 (2005)]. Thus, these studies with VPA did not resolve the potential of HDACi to eliminate the virus.

WO 2008/097654 discloses the use of SAHA for the treatment of HIV infection; SAHA is a HDACi, not having a N-hydroxy-benzamide structure, which is available in the market as Vorinostat or Zolinza. In WO 2008/097654 (example 2 and FIG. 1) SAHA is indicated to induce the HIV-1 gene expression in the ACH-2 cell line, with an $EC_{50}$ of 0.632 μM.

The Zolinza package leaflet indicates that a possibly effective circulating concentration of SAHA for treating patients affected by Cutaneous T-Cell Lymphoma may be obtained with a dosage of 400 mg/day. However, at this dosage SAHA may cause numerous, serious adverse effects such as diarrhoea, tiredness, nausea, thrombocytopenia, anorexia and dysgeusia. Furthermore, according to the information on the Zolinza package leaflet, SAHA is mutagenic in vitro in the bacterial back-mutation assays (Ames test), it causes chromosome aberrations in vitro in Chinese Hamster Ovary (CHO) cells and it increases the incidence of micronucleated erythrocytes when administered to mice (Mouse Micronucleus Assay).

It is thus clear that there arises the need for new HIV-1 expression induction agents, possibly HDAC inhibitors, which are more active and less toxic, preferably both more active and less toxic, than the HDAC inhibitors which are already known to be effective at inducing the HIV-1 gene expression.

DESCRIPTION OF THE INVENTION

It has now been discovered, and this constitutes an aspect of the present invention, that diethyl-[6-(4-hydroxycarbamoyl-phenylcarbamoyloxymethyl)-naphtalen-2-yl-methyl]-ammonium chloride, preferably in monohydrate form, more preferably in monohydrate crystal form (ITF2357, Givinostat), is capable of inducing the HIV-1 gene expression, in the ACH-2 cell line, at a concentration preferably between 125 and 250 nM.

ITF2357 revealed to be non-mutagenic [Monzani, V M et al. presented at EUROTOX 2007, 44$^{th}$ Congress of toxicology, poster G33]; therapeutic circulating concentrations between 125 and 250 nM may be easily obtained, in the clinical treatment, by administering 50-200 mg of ITF2357. The dosages within this range were used in numerous clinical studies and the detected toxic effects were extremely low; an equivalent dose of 1.5 mg/kg/day was administered to children with systemic onset juvenile idiopathic arthritis (SOJIA) with encouraging results and without detection of any toxic effect [Vojinovic, J. et al. presented at The 72$^{nd}$ annual meeting of the American College of Rheumatology, San Francisco, Calif., 29 Oct. 2008].

It was thus found, and this is a second aspect of the invention, that some HDAC inhibitors which are 4-amino-N-hydroxy-benzamide derivatives (which include ITF2357) may be extremely effective at inducing the HIV gene expression at concentrations that do not reveal any considerable toxicity; this seems to be in contrast with the previous opinions [Shehu-Xhilaga, M. et al. *AIDS* 23, 2047 (2009)] which suggest that the two effects, HIV gene induction and toxicity, may depend on the same structural and/or mechanistic reasons.

It has also been found, and this is a third aspect of the invention, that some of such 4-amino-N-hydroxy-benzamide derivatives, capable of inhibiting HDAC enzymes, are even more potent than ITF2357 at inducing the HIV-1 gene expression, in the ACH-2 cell line, at a concentration between 125 and 250 nM. Purely by way of example, 4-(2(S)-benzoylamino-3-naphtalen-2-yl-propionylamino)-N-hydroxy-benzamide (compound g) and benzo[1,3]dioxole-5-carboxylic acid [1(S)-(4-hydroxycarbamoyl-phenylcarbamoyl)-2-naphtalen-2-yl-ethy]-amide (compound t), both described in example 2 of the aforementioned WO 2006/003068, induce, in ACH-2 cells, at 250 nM, an increase of the HIV expression 30 times higher with respect to the 15 times higher increase obtained with the same concentration of ITF2357.

The chemical structures of:
diethyl-[6-(4-hydroxycarbamoyl-phenylcarbamoyloxymethyl)-naphtalen-2-yl-methyl]-ammonium chloride;
4-(2-(S)-benzoylamino-3-naphtalen-2-yl-propionylamino)-N-hydroxy-benzamide (compound g); and
benzo[1,3]dioxole-5-carboxylic acid [1(S)-(4-hydroxycarbamoyl-phenylcarbamoyl)-2-naphtalen-2-yl-ethyl]-amide (compound t); are shown hereinafter.

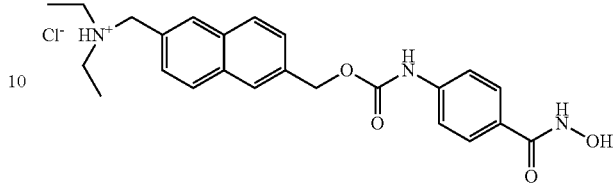

Diethyl-[6-(4-hydroxycarbamoyl-phenylcarbamoyloxymethyl)-naphtalen-2-yl-methyl]-ammonium chloride

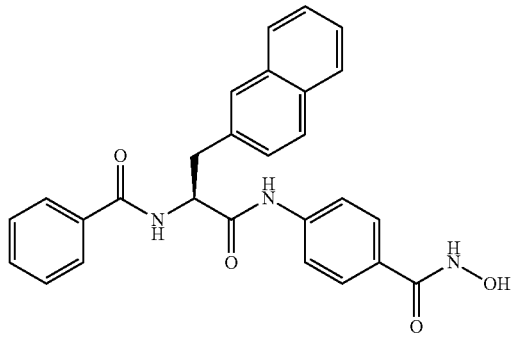 [SMILES: O=C(NO)c1ccc(NC(=O)[C@H](Cc2ccc3ccccc3c2)NC(=O)c2ccccc2)cc1]

Compound g

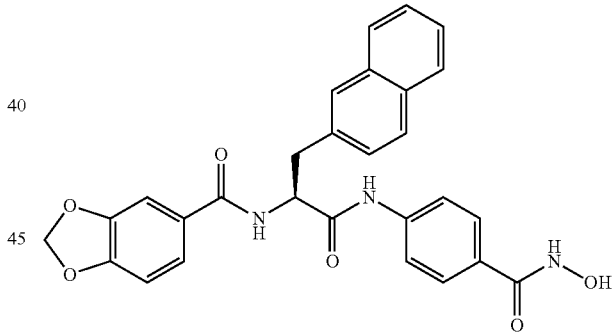

Compound t

Thus, the object of the present invention is represented by a compound of general formula I for use in the treatment of HIV infections, preferably HIV-1 infections,

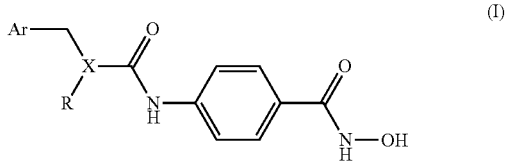

wherein:
X is O, CH or it is absent;
Ar is aryl or saturated, unsaturated or partially unsaturated mono-, di-, tricyclic carbocyclic residue, or a saturated, unsaturated or partially unsaturated mono-, di-, tricyclic heterocyclic residue comprising one or more heteroatoms selected from among N, S and O; said carbocyclic or heterocyclic aryl residue being optionally substituted with one or more identical or different halogens, $C_1$-$C_4$ alkyl, $C_1$-$C_4$ alkoxyl, $C_1$-$C_4$ haloalkyl, alkylsulfonyl, cycloalkyl, (cycloalkyl)alkyl, alkanoyl, amino, ($C_1$-$C_4$) mono- or dialkylamino, ($C_1$-$C_4$) aminoalkyl mono- or disubstituted with $C_1$-$C_4$ alkyl, carboxy, $C_1$-$C_4$ alkoxylcarbonyl, mercaptoalkoxy, mercaptophenoxy, nitro, cyano, oxo, perfluoroalkoxy, perfluoroalkyl, phenyl, phenoxy, phenylalkoxy, benzoyloxy, phenylalkyl, benzoyl, phenylsulfonyl and hydroxy;

R is absent or it is an $R^1$—CO—NH-residue;

wherein $R^1$ is aryl, arylalkyl, linear or branched $C_1$-$C_4$ alkyl, or saturated, unsaturated or partially unsaturated mono-, di-, tricyclic carbocyclic residue, or a saturated, unsaturated or partially unsaturated mono-, di-, tricyclic heterocyclic residue comprising one or more heteroatoms selected from among N, S and O; said aryl, arylalkyl, linear or branched $C_1$-$C_4$ alkyl, carbocyclic or heterocyclic residue optionally being selected, with one or more residues, mutually identical or different, from among: halogen, $C_1$-$C_4$ alkyl, $C_1$-$C_4$ alkoxyl, $C_1$-$C_4$ haloalkyl, alkylsulfonyl, cycloalkyl, (cycloalkyl)alkyl, alkanoyl, amino, ($C_1$-$C_4$) mono- or dialkylamino, ($C_1$-$C_4$) aminoalkyl mono- or disubstituted with $C_1$-$C_4$ alkyl, carboxy, $C_1$-$C_4$ alkoxylcarbonyl, mercaptoalkoxy, mercaptophenoxy, nitro, cyano, oxo, perfluoroalkoxy, perfluoroalkyl, phenyl, phenoxy, phenylalkoxy, benzoyloxy, phenylalkyl, benzoyl, phenylsulfonyl and hydroxy.

According to a preferred embodiment of the invention,

X is O or CH, and

Ar is 6-diethylaminomethyl-naphtalen-2-yl or naphtalen-2-yl.

The most preferred compounds being:

Diethyl-[6-(4-hydroxycarbamoyl-phenyl-carbamoyloxymethyl)-naphtalen-2-yl-methyl]-ammonium chloride, preferably in monohydrate form, more preferably in monohydrate crystal form;

4-(2-(S)-benzoylamino-3-naphtalen-2-yl-propionylamino)-N-hydroxy-benzamide; and/or benzo[1,3]dioxole-5-carboxylic acid [1(S)-(4-hydroxycarbamoyl-phenylcarbamoyl)-2-naphtalen-2-yl-ethyl]-amide.

The compound of formula I is mainly intended for administration to a human, preferably to obtain a blood concentration between 125 and 250 nM; preferably, such compound is administered at a dosage ranging from 50 to 200 mg/day, more preferably from 100 to 200 mg/day.

According to an embodiment it is administered at a dosage ranging from 50 mg twice a day to 200 mg once a day.

According to another embodiment, it is administered in combination and/or in temporal proximity with at least one anti-retroviral agent; preferred anti-retroviral agents include nucleoside reverse transcriptase inhibitors, non-nucleoside reverse transcriptase inhibitors, protease inhibitors, fusion inhibitors, entry inhibitors, integrase inhibitors, co-receptor antagonists, viral adsorption inhibitors, viral specific transcription inhibitors and/or cyclin dependent kinase inhibitors; the most preferred anti-retroviral agents being efavirenz, indinavir sulfate and/or raltegravir potassium.

EXAMPLE 1

Induction of the HIV-1 Expression in the ACH-2 Cell Line

ACH2 cells were obtained through AIDS Research and Reference Reagent Program, Division of AIDS, National Institute of Allergy and Infectious Diseases, National Institutes of Health, Bethesda, Md. The cells were cultured in flasks, washed in RPMI and resuspended in RPMI/10% FCS at a concentration of $2 \times 10^6$ cells/mL. 250 µL of cells, 200 µL of media and 50 µL of HDAC inhibitors solution at various concentrations (from 0 to 250 nM), containing 0.01% DMSO, were divided into aliquotes in a 48-wells polystyrene tissue culture plate (Falcon, Lincoln Park, N.J.). After 24 hours of incubation at 37° C./5% $CO_2$, 50 µL of supernatant were removed for the cytotoxicity assay of the lactate dehydrogenase (LDH) and Triton-X-100 (0.5% vol/vol final concentration) were added to each culture. The p24 assays of the lysates were performed immediately.

The cellular death as determined by the LDH activity after 24 hours was not considerably different in the cells exposed to HDAC inhibitors with respect to the non-treated cells.

p24 was measured using specific antibodies immobilized on magnetic beads as previously described [Nold M. F. et al. *J. Immunol.* 181, 557 (2008)]. The levels of p24 for each experiment without HDAC inhibitors were fixed at 1.0 and the increase values by the number of times for each experiment and each analogous were calculated. The results are shown in the table below.

TABLE 1 increase of the number of times in the level of p24 expressed in the presence of inhibitors with respect to the level obtained in the control

| Conc (nM) | ITF2357 | Compound g | Compound t |
|---|---|---|---|
| 31 | 1 | 2 | 1 |
| 63 | 1 | 3 | 2 |
| 125 | 2 | 10 | 10 |
| 250 | 15 | 27 | 33 |

EXAMPLE 2

Inhibition of Histone Deacetylase Isoforms

Recombinant human enzymes were acquired from BPS Biosciences (CA, USA). Isoforms of Class I HDAC1, 2, 3; HDAC6, 10 of Class IIb and Class IV HDAC11 were tested using the Fluor-de-Lys fluorogenic synthetic substrate (Enzo Life Sciences, Plymouth Meeting, Pa.). Isoforms of Class IIa HDAC4, 7, 9 were tested using the Boc-L-Lys(Tfa)-MCA (TFAL) derivative, described as a specific substrate for these enzymes [Jones P. et al. *Bioorg Med Chem Lett.* 18, 3456 (2008)]. The recombinant human HDAC8 assay was performed using HDAC8 Fluorimetric Drug Discovery Kit (Enzo) according to the manufacturer instructions. Each inhibitor was dissolved in DMSO and then further diluted in an assay buffer. Concentrations of DMSO lower than 0.5% do not affect the activity of the assay. The assays were performed by pre-incubating each enzyme with the inhibitors for 15 minutes at 37° C. The reaction was started by adding the substrate at 37° C. and allowed to proceed for 60 minutes. The fluorescent signal was generated by adding 50 µL of a twice concentrated developer solution 2 (Enzo) containing trichostatin A 4 µM. The generated fluorescence was detected at 355 nm (excitation) and 460 nm (emission) wavelengths.

The results, expressed as $IC_{50}$ (concentration required to reduce the enzymatic activity by 50%), are shown in the table below (the SAHA values were also measured and they are shown in the table).

TABLE 2

| | values of IC$_{50}$ (nM) for the inhibition of each HDAC isoform | | | | | | | | | |
|---|---|---|---|---|---|---|---|---|---|---|
| ITF | hHD1 | hHD2 | hHD3 | hHD4 | hHD6 | hHD7 | hHD8 | hHD9 | hHD10 | hHD11 |
| ITF2357 | 116.7 | 119.3 | 124.0 | 724 | 411.0 | 612.8 | 940.0 | 518.0 | 351.0 | 307.0 |
| Compound g | 54.7 | 12.0 | 245.8 | 3,107 | 3,622 | 2,021 | 491.9 | 4,153 | 132.1 | 441.4 |
| Compound t | 71.5 | 29.5 | 107.2 | >10,000 | 618.2 | 8,621 | 161.6 | >10,000 | 275.8 | 336.3 |
| SAHA | 77.9 | 287.4 | 166.9 | >10,000 | 471.0 | >10,000 | 1,676 | >10,000 | 152.0 | 187.8 |

The invention claimed is:

1. A method for treating a HIV infection comprising administering to a patient in need of such a compound selected from 4-(2(S)-benzoylamino-3-naphthalen-2-yl-propionylamino)-N-hydroxy-benzamide and benzo[1,3]dioxole-5-carboxylic acid [1(S)-(4-hydroxycarbamoyl-phenylcarbamoyl)-2-naphthalen-2-yl-ethyl]-amide, wherein said compound is administered in combination and/or in temporal proximity with at least one anti-retroviral agent.

2. The method according to claim 1, wherein said HIV infection is a HIV-1 infection.

3. The method according to claim 1, wherein the patient is a human.

4. The method according to claim 3, wherein the administration is at a dosage ranging from 50 to 200 mg/day.

5. The method according to claim 4, wherein the administration is at a dosage ranging from 100 to 200 mg/day.

6. The method according to claim 3, wherein the administration is at a dosage ranging from 50 mg twice a day to 200 mg once a day.

7. The method according to claim 3, wherein the human has a blood concentration between 125 and 250 nM.

8. The according to claim 1, wherein the administration is in combination with said at least one anti-retroviral agent.

9. The method according to claim 8, wherein said at least one anti-retroviral agent is selected from the group consisting of nucleoside reverse transcriptase inhibitors, non-nucleoside reverse transcriptase inhibitors, protease inhibitors, fusion inhibitors, entry inhibitors, integrase inhibitors, co-receptor antagonists, viral adsorption inhibitors, viral specific transcription inhibitors and cyclin dependent kinase inhibitors.

10. The method according to claim 9, wherein said anti-retroviral agent is selected from the group consisting of efavirenz, indinavir sulfate and raltegravir potassium.

* * * * *

UNITED STATES PATENT AND TRADEMARK OFFICE
CERTIFICATE OF CORRECTION

PATENT NO. : 8,637,702 B2  Page 1 of 1
APPLICATION NO. : 13/393863
DATED : January 28, 2014
INVENTOR(S) : Dinarello et al.

It is certified that error appears in the above-identified patent and that said Letters Patent is hereby corrected as shown below:

In the Claims

Claim 1, Column 7, line 14, after "such" insert --treatment--.

Signed and Sealed this
Twenty-seventh Day of May, 2014

Michelle K. Lee
*Deputy Director of the United States Patent and Trademark Office*